(12) United States Patent
Blondel et al.

(10) Patent No.: US 9,447,216 B2
(45) Date of Patent: Sep. 20, 2016

(54) COMB POLYMERS WHICH CAN BE USED IN COSMETICS AND DETERGENTS

(71) Applicant: S.P.C.M. SA, Andrezieux Boutheon (FR)

(72) Inventors: Frédéric Blondel, Lezigneux (FR); Antonin Sanna, Saint Etienne (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 59 days.

(21) Appl. No.: 14/368,664

(22) PCT Filed: Jan. 14, 2013

(86) PCT No.: PCT/FR2013/050087
§ 371 (c)(1),
(2) Date: Jun. 25, 2014

(87) PCT Pub. No.: WO2013/107976
PCT Pub. Date: Jul. 25, 2013

(65) Prior Publication Data
US 2014/0378639 A1   Dec. 25, 2014

(30) Foreign Application Priority Data

Jan. 16, 2012   (FR) ..................... 12 50380

(51) Int. Cl.
| | | |
|---|---|---|
| *C08F 220/28* | (2006.01) | |
| *C08F 226/04* | (2006.01) | |
| *C11D 3/37* | (2006.01) | |
| *A61Q 5/02* | (2006.01) | |
| *A61K 8/81* | (2006.01) | |
| *A61Q 19/10* | (2006.01) | |
| *C08F 290/06* | (2006.01) | |

(52) U.S. Cl.
CPC ............. *C08F 220/28* (2013.01); *A61K 8/817* (2013.01); *A61Q 5/02* (2013.01); *A61Q 19/10* (2013.01); *C08F 226/04* (2013.01); *C08F 290/062* (2013.01); *C11D 3/3769* (2013.01); *A61K 2800/5426* (2013.01); *C08F 2220/282* (2013.01); *C08F 2220/285* (2013.01)

(58) Field of Classification Search
CPC ..................... A61K 8/817; A61K 2800/5426; A61Q 19/10; A61Q 5/02; C08F 220/28; C08F 226/04; C08F 290/062; C08F 2220/282; C08F 2220/285; C11D 3/3769
USPC .......................................... 526/310
See application file for complete search history.

(56) References Cited

U.S. PATENT DOCUMENTS

2008/0292577 A1 * 11/2008  Mougin ............... A61K 8/8152
                                                        424/70.17

FOREIGN PATENT DOCUMENTS

| AU | 2004200189 B2 | 11/2006 | |
|---|---|---|---|
| EP | 0372546 A2 | 6/1990 | |
| EP | 1765893 A2 | 3/2007 | |
| EP | 1769011 A2 | 4/2007 | |
| FR | 2962034      * | 1/2012 | ............... A61K 8/90 |
| FR | 2962034 A1 | 1/2012 | |
| JP | H07285831 A | 10/1995 | |
| JP | 2000302649 A | 10/2000 | |
| JP | 2002284627 A  * | 10/2002 | ............... A61K 7/00 |
| JP | 2002322219 A | 11/2002 | |
| JP | 2003055164 A | 2/2003 | |
| WO | 2006013268 A2 | 2/2006 | |

OTHER PUBLICATIONS

International Search Report for PCT/FR2013/050087 dated Mar. 20, 2013.

* cited by examiner

*Primary Examiner* — Ling Choi
*Assistant Examiner* — Chun-Cheng Wang
(74) *Attorney, Agent, or Firm* — Heslin Rothenberg Farley & Mesiti P.C.

(57) ABSTRACT

A water-soluble copolymer comprising, by mass relative to the total mass of the copolymer:
  5 to 45% of at least one cationic monomer whose cationicity comes exclusively from one or more quaternary ammonium functional groups;
  50 to 95% of at least one monomer of formula (I);

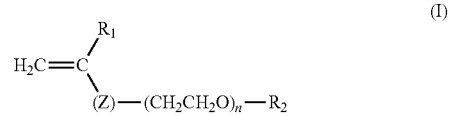

in which:
  $R_1$ is a hydrogen atom or a methyl radical;
  Z is a divalent group —C(=O)—O—, or —C(=O)—NH—;
  n is an integer between 2 and 200;
  $R_2$ is a hydrogen atom or a carbon-containing radical which is saturated or unsaturated, optionally aromatic, linear, branched or cyclic, comprising 1 to 30 carbon atoms, and from 0 to 4 heteroatoms chosen from the group comprising O, N and S;
the copolymer having a cationic charge density of between 0.3 and 2.6 meq/g.

17 Claims, No Drawings

COMB POLYMERS WHICH CAN BE USED IN COSMETICS AND DETERGENTS

CROSS REFERENCE TO RELATED APPLICATIONS

This application is a national stage filing under section 371 of International Application No. PCT/FR2013/050087, filed on Jan. 14, 2013, and published on Jul. 25, 2013 as WO 2013/107976 A1, and claims priority to French Application No. 1250380 filed on Jan. 16, 2012. The entire disclosures of each of the prior applications are hereby incorporated herein by reference.

The present invention relates to the technical field of polymers with a "comb" structure. More specifically, the invention relates to the technical field of cationic comb polymers having hydrophilic pendant chains. These comb polymers find applications in particular in the fields of cosmetics and detergents.

A "comb" polymer has a structure similar to that of a comb. In other words, it comprises a principal chain to which side chains are attached which may be different in nature and of variable length. For example, these side chains may have hydrophilic and/or hydrophobic properties. They may in particular be of the ethylene oxide, propylene oxide and alkyl type, and the like, with lengths of 2 to 500 units and preferably 5 to 200 units in the case of a pendant chain of the polyethylene oxide type.

The comb polymers of the prior art comprise in particular polymers based on polyethylene glycol(meth)acrylate (PEGMA) units and on cationic units.

The document EP372546 describes copolymers based on PEGMA, monomers of the $C_1$-$C_8$ alkyl(meth)acrylamide type, and optionally cationic monomers.

The document JP2002-322219 describes polymers containing PEGMA units in association with hydrophobic monomers based on polypropylene glycol (PPO) or poly (tetramethylene oxide), and cationic monomers.

The document JP2003-055164 describes cross-linked polymers containing units of the PEGMA type; however, these polymers are cross-linked, which makes controlling their synthesis more complicated.

The document JP2000-302649 also describes a hair composition comprising a polymer based on cationic monomers having quaternary amine groups, monomers with a polyether group, in particular of the PEG (polyethylene glycol) or PPO type, and optionally hydrophobic monomers (for example stearyl methacrylate).

The document JP07-285831 describes hair compositions containing a polymer based on PEGMA-type monomers combined with ionic, cationic or amphoteric monomers, and additional monomers of the $C_1$-$C_{24}$ alkyl(meth)acrylate type, which are mainly hydrophobic.

The documents EP1769011 and EP1765893 describe polymers mainly consisting of cationic units and PEGMA units.

The document WO2006/013268 describes polymers comprising at least one monomer of the PEG (meth)acrylate type combined with a monomer having a cationic (cationic, amphoteric or cationic and anionic) character.

The document AU 2004 200 189 describes a polymer which may comprise a monomer of the PEG acrylate type combined with a monomer which may be cationic but which does not comprise a quaternary ammonium functional group.

The document FR 2 962 034 describes a polymer containing a monomer of the PEG methacrylate type combined with a monomer not comprising a quaternary ammonium functional group.

As already stated, the fields of application of comb polymers are in particular cosmetics and detergents. They may therefore be present as a conditioner in compositions of body and hair products, or as an agent for promoting deposition in laundry detergents.

However, the presence of anionic species in the final formulations introduces incompatibilities with cationic polymers.

The incompatibility between a cationic polymer and an anionic species, owing to their opposite charges, can be reflected by the appearance of a precipitate, i.e. an insoluble aggregate resulting from the coalescence of colloidal particles in suspension. Generally, the formation of a precipitate is of course contraindicated in formulations of the shampoo, laundry detergent or softener type.

The applicant has developed polymers which make it possible in particular to overcome the drawbacks associated with incompatibilities between anionic species and cationic polymers.

The present invention thus relates to polymers which, once incorporated into a cosmetic or detergent composition, make it possible to prevent the formation of precipitates resulting from the ionic attraction between two compounds of opposite charge.

The applicant has demonstrated that this technical problem can be solved, not only by limiting the proportion of cationic monomer(s) in the polymer to less than 50% by mass, but also by combining the cationic monomer(s) with at least one monomer which has a pendant chain, thus making it possible to adjust the cationic charge density of the polymer.

The subject of the present invention is therefore a water-soluble copolymer with ethylene units, comprising, as a percentage by mass relative to the total mass of the copolymer:

5 to 45% of at least one cationic monomer whose cationicity comes exclusively from one or more quaternary ammonium functional groups;

50 to 95% of at least one monomer of formula (I); advantageously from 55 to 95%;

$$H_2C=C\begin{matrix}R_1\\ \\(Z)-(CH_2CH_2O)_n-R_2\end{matrix} \quad (I)$$

in which:
$R_1$ is a hydrogen atom or a methyl radical;
Z is the divalent group —C(=O)—O—, or —C(=O)—NH—;
n is an integer between 2 and 200;
$R_2$ is a hydrogen atom or a carbon-containing radical which is saturated or unsaturated, optionally aromatic, linear, branched or cyclic, comprising 1 to 30 carbon atoms, comprising from 0 to 4 heteroatoms chosen from the group comprising O, N and S.

Advantageously, n is between 7 and 45.

In addition, according to one essential characteristic of the invention, the cationicity of the copolymer is advantageously between 0.3 and 2.6 meq/g, preferably between 0.5 and 1.5 meq/g.

The term "water-soluble" denotes a copolymer which may be dissolved in an aqueous solution, in an amount of at least 50 g/L at 25° C., without leaving insoluble particles.

The cationicity or cationic charge density corresponds to the cationic equivalent number per unit of mass.

In other words, in the case where the copolymer comprises a cationic monomer A, and a noncationic monomer B, it is determined according to the following formula:

$$\text{cationicity(meq/g)} = (100 \times \% A)/(\% A \times Mw_A + \% B \times Mw_B)$$

in which:
- % A represents the molar percentage of the cationic monomer A;
- % B represents the molar percentage of the noncationic monomer B;
- $Mw_A$ represents the molar mass of the cationic monomer A;
- $Mw_B$ represents the molar mass of the noncationic monomer B.

The cationic charge density therefore depends on the proportions of monomers and their respective molar masses. Consequently, at equivalent monomer ratio, two polymers do not necessarily have the same cationic charge density considering the molar mass of each of the monomers.

According to a particular embodiment, the copolymer consists of, as percentage by mass relative to the total mass of the copolymer:
- 5 to 45% of at least one cationic monomer whose cationicity comes exclusively from one or more quaternary ammonium functional groups;
- 55 to 95% of at least one monomer of formula (I).

According to a particular embodiment, the copolymer has cationic charges which come solely from quaternary ammonium functional groups. In other words, according to this particular embodiment, the cationicity of the cationic monomer(s) contained in the copolymer is exclusively due to the presence of quaternary ammonium functional groups. According to this embodiment, all of the cationic charges of the copolymer come from quaternary ammonium functional groups.

According to a preferred embodiment, in the monomer of formula (I), $R_2$ is either a hydrogen atom; a benzyl radical; a phenyl radical optionally substituted with at least one $C_1$-$C_{12}$ alkyl; a linear or branched $C_1$-$C_{30}$ alkyl radical, optionally comprising at least one cyclic group, and optionally at least one aromatic group, in particular as $C_1$-$C_{22}$, or even as $C_2$-$C_{16}$, optionally comprising 1 to 4 heteroatoms chosen from O, N and S. Mention may be made in particular of the methyl, ethyl, propyl, benzyl, ethylhexyl, lauryl, stearyl and behenyl radicals.

Among the preferred monomers of formula (I), there may be mentioned:
- poly(ethylene glycol)(meth)acrylate in which $R_1$=H or $CH_3$; Z=C(=O)—O—; $R_2$=H; with n=2 to 200;
- methyl-poly(ethylene glycol)(meth)acrylate, also called methoxy-poly(ethylene glycol)(meth)acrylate, in which $R_1$=H or $CH_3$; Z=C(=O)—O—; and $R_2$=$CH_3$; with n=2 to 200;
- alkyl-poly(ethylene glycol)(meth)acrylates in which $R_1$=H or $CH_3$; Z=C(=O)—O—; and $R_2$=$C_1$-$C_{30}$ alkyl; with n=2 to 200;
- phenyl-poly(ethylene glycol)(meth)acrylates, also called poly(ethylene glycol)phenyl ether(meth)acrylate, in which $R_1$=H or $CH_3$; Z=C(=O)—O—; and $R_2$=phenyl; with n=2 to 200.

The monomers of formula (I) which are quite particularly preferred may be chosen from the group comprising poly(ethylene glycol)(meth)acrylates and methylpoly(ethylene glycol)(meth)acrylates, preferably those having a molar mass of between 80 and 8000 g/mol, in particular between 300 and 2000 g/mol.

Among the commercial monomers, there may be mentioned:
- polyethylene glycol 8000 to 4000 methacrylates marketed by Monomer & Polymer Dajac laboratories;
- poly(ethylene glycol) methacrylates, of molar mass 5000 g/mol, available from EVONIK under the trade name VISIOMER®;
- hydroxy-poly(ethylene glycol) methacrylates marketed by CLARIANT under the trade name POLYGLYKOL® MA.

The cationic monomer(s) which have a quaternary ammonium functional group and which may be used in the context of the invention may be chosen in particular from monomers of the acrylamide, acrylic, vinyl, allyl or maleic type having a quaternary ammonium functional group. Mention may be made, in particular and without limitation, of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC) and methacrylamidopropyltrimethylammonium chloride (MAPTAC).

According to a particular embodiment, the copolymer which is the subject of the present invention also comprises at least one nonionic monomer distinct from that corresponding to formula (I) above. Advantageously, this additional nonionic monomer represents less than 25% by mass of the copolymer, advantageously from 5 to 25%.

Thus, according to a particular embodiment, the copolymer which is the subject of the invention may consist of, as percentage by mass relative to the total mass of the copolymer:
- 5 to 45% of at least one cationic monomer whose cationicity comes exclusively from one or more quaternary ammonium functional groups;
- 50 to 95% of at least one monomer of formula (I); advantageously from 55 to 95%;
- 5 to 25% of at least one nonionic monomer distinct from the monomer of formula (I).

The nonionic monomer(s) which may be used in the context of the invention may be chosen in particular from the group comprising water-soluble vinyl monomers. Preferred monomers belonging to this class are, for example, acrylamide, methacrylamide, N-isopropylacrylamide, N,N-dimethylacrylamide and N-methylolacrylamide. Also, use may be made of N-vinylformamide, N-vinylacetamide, N-vinylpyridine and N-vinylpyrrolidone, acryloylmorpholine (ACMO) and diacetone acrylamide. A preferred nonionic monomer is acrylamide.

According to some embodiments, in addition to the above monomers, the water-soluble copolymer(s) may also comprise one or more hydrophobic monomers chosen in particular from monomers of the acrylamide, acrylic, vinyl, allyl or maleic type having a pendant hydrophobic functional group preferably chosen from acrylamide derivatives such as N-alkylacrylamides, for example, diacetone acrylamide, N-tert-butylacrylamide, octylacrylamide, and N,N-dialkylacrylamides such as N,N-dihexylacrylamide and acrylic acid derivatives such as alkyl acrylates and methacrylates. Also, use may be made of derivatives of vinyl monomers such as N-vinylformamide, N-vinylacetamide, N-vinylpyridine, and N-vinylimidazole.

In general, the polymers of the invention do not require the development of a specific polymerization process. Indeed, they may be obtained according to all the polymerization techniques well known to a person skilled in the art. These may be in particular solution polymerization; gel polymerization; precipitation polymerization; (aqueous or inverse) emulsion polymerization; suspension polymerization; or micellar polymerization.

The polymer may be provided in liquid or solid form when its preparation includes a drying step such as spray-drying, drying on a drum or alternatively microwave drying.

As already stated, compared with the polymers of the prior art, the polymer developed by the applicant exhibits improved compatibility with anionic species.

The term "anionic species" is understood to mean all the macromolecular elements having an anionic character which are commonly present in cosmetic or detergent type formulations and the like.

Consequently, the present invention also relates to the use of the copolymer described above in a cosmetic or detergent formulation.

Without limitation, these ionic species may be:

(i) Anionic surfactants among which there may be mentioned, alone or mixed, salts (in particular alkali metal salts, in particular sodium salts, ammonium salts, amino salts, salts of amino alcohols or magnesium salts) of the following compounds: alkyl sulfates, alkyl ether sulfates, alkyl amido ether sulfates, alkyl aryl polyether sulfates, monoglyceride sulfates, alkyl sulfonates, alkyl phosphates, alkyl amide sulfonates, alkyl aryl sulfonates, alpha-olefin sulfonates, paraffin sulfonates, alkyl sulfosuccinates, alkyl ether sulfosuccinates, alkyl amide sulfosuccinates, alkyl sulfosuccinamates; alkyl sulfoacetates, alkyl ether phosphates, acyl sarcosinates, acyl isethionates, N-acyltaurates. The alkyl or acyl radical of all these various compounds preferably comprises from 8 to 24 carbon atoms, while the aryl radical preferably denotes a phenyl or benzyl group.

Mention may also be made of the salts of fatty acids such as the salts of oleic, ricinoleic, palmitic and stearic acids, the salts of acids of copra oil or of hydrogenated copra oil; the salts of acyl lactylates in which the acyl radical comprises 8 to 20 carbon atoms; the salts of alkyl D-galactoside uronic acids as well as the salts of polyoxyalkylenated ($C_6$-$C_{24}$) alkyl ether carboxylic acids, the salts of polyoxyalkylenated ($C_6$-$C_{24}$)alkyl aryl ether carboxylic acids, the salts of polyoxyalkylenated ($C_6$-$C_{24}$)alkyl amidoether carboxylic acids, in particular those comprising from 2 to 50 ethylene oxide groups; and mixtures thereof.

(ii) Anionic polyelectrolytes comprising at least one monomer having an acrylic, vinyl, maleic, fumaric or allyl functionality and containing a carboxy, phosphonate or sulfonate group, or another group having an anionic charge. There may in particular be: acrylic acid, methacrylic acid, itaconic acid, crotonic acid, maleic acid, fumaric acid, and monomers of the strong acid type having for example a functional group of the sulfonic acid or phosphonic acid type such as 2-acrylamido-2-methylpropanesulfonic acid, vinylsulfonic acid, vinylphosphonic acid, allylsulfonic acid, allylphosphonic acid. There may also be silicone-based polyelectrolytes comprising one or more carboxylate, sulfate, sulfonate, phosphate or phosphonate groups, or derivatives thereof.

(iii) Natural polymers having an anionic character which may be chosen from the group comprising polysaccharides such as cellulose, starch, guar gum, guar gum hemicellulose, gum arabic, glucomannan, carob gum, pullulan, curdlan, xanthan gum, gellan gum, carrageenan gum, dextran gum, tragacanth gum, welan gum, rhamsan gum, hyaluronic acid, inulin, pectin, lignin, chitin, alginate, agar agar or derivatives thereof.

The invention and the advantages resulting therefrom will emerge more clearly from the following figures and examples given so as to illustrate the invention and without limitation.

EXAMPLES OF IMPLEMENTATION OF THE INVENTION

A/ Preparation of the Copolymers

1/ DADMAC/PEG 2000 MA (75/25) Copolymer
(Polymer A)

Polymer A comprises 75 mol % of DADMAC monomer and 25 mol % of polyethylene glycol methacrylate, i.e. 20% by mass of DADMAC and 80% by mass of polyethylene glycol methacrylate.

The following are loaded in a reactor equipped with a mechanical stirring system, a condenser, a thermometer and a nitrogen inlet:

122 g of DADMAC (Flocryl, SNF)

585 g of PEG 2000 MA (Polyglykol® MA 2000, Clariant). It is a polyethylene glycol methacrylate whose molar mass is 2000 g/mol.

1.75 g of sodium hypophosphite 261 g of water 0.03 g of EDTA (ethylenediaminetetraacetic acid)

The reaction medium is deoxygenated with a nitrogen stream, and heated at 80° C.

Separately, an initiator solution is prepared by introducing 0.35 g of 2,2'-azobis(2-amidinopropane)dihydrochloride (V50, Wako) in 30 g of water.

When the temperature of the medium has reached 80° C., gradual addition of the initiator solution is started. The solution is added for 180 minutes and then the medium is kept at 80° C. for 120 additional minutes in order to complete the polymerization.

The mixture is allowed to return to room temperature and then the pH is adjusted to between 5 and 7 using an aqueous NaOH or citric acid solution at 50% by mass.

The product obtained is a liquid solution whose polymer concentration is 40% by mass relative to the mass of the solution. The solution has a viscosity of 300 cps (Brookfield LVT, spindle 3, 30 rpm). Polymer A has a comb structure. Its cationic charge density is 1.15 meq/g.

2/ DADMAC/PEG 2000 MA (98/2) Copolymer
(Polymer B) (Prior Art)

Polymer B comprises 98 mol % of DADMAC monomer and 2 mol % of polyethylene glycol methacrylate, i.e. 80% by mass of DADMAC and 20% by mass of polyethylene glycol methacrylate.

Using the same procedure as that described in example 1, a DADMAC/PEG 2000 MA copolymer containing 2 mol % of PEG 2000 MA is prepared. In this case, the following quantities are used:

499 g of DADMAC (Flocryl, SNF)

146 g of PEG 2000 MA (Polyglykol® MA 2000, Clariant)

3.55 g of sodium hypophosphite 315 g of water 0.03 g of EDTA 1.1 g of azobis(2-amidinopropane)dihydrochloride (V50, Wako) in 30 g of water.

The product obtained is a liquid having a polymer concentration of 40% by mass relative to the mass of the product, and a viscosity of 1700 cps (Brookfield LVT, spindle 3, 30 rpm). The polymer has a comb structure. Its cationic charge density is 4.26 meq/g.

3/ DADMAC Homopolymer (Polymer C) (Prior Art)

Using the same procedure as that described in example 1, a DADMAC homopolymer is prepared. In this case, the following quantities are used:

625 g of DADMAC (Flocryl, SNF)

4.36 g of sodium hypophosphite 339 g of water 0.03 g of EDTA 1.34 g of V50 in 30 g of water.

The product obtained is a liquid solution whose polymer concentration is 40% by mass relative to the mass of the solution. The solution has a viscosity of 200 cps (Brookfield LVT, spindle 3, 30 rpm). Polymer B has a comb structure. Its cationic charge density is 6.1 meq/g.

B/ Study of the Compatibility Between the Polymers and Anionic Polyelectrolytes

Method

The compatibility between cationic polymers and anionic polyelectrolytes is evaluated by titration.

The following method is used:

50 g of an aqueous solution at 20% by mass of anionic surfactant (TEA lauryl sulfate, TEA=triethanolamine) is prepared and stirred in a glass beaker;

with stirring, various additions of cationic polymer are carried out and the appearance of the solution thus prepared is observed.

The maximum mass of cationic product that can be added before the appearance of a precipitate or of a cloudiness reflecting precipitation is determined.

The quantity of cationic polymer introduced is then linked to a cationic charge introduced into the system.

Results

The compatibility between the polymers (A, B, C and polyquaternium 7) and TEA lauryl sulfate (solution at 20% by mass) was evaluated. The results of the titration are given in the table below:

| Cationic polymer | Charge density of the polymer (meq/g) | Anionic surfactant (solution at 20%) | Quantity of polymer added (g of dry polymer) | Appearance | Total cationicity (meq) |
|---|---|---|---|---|---|
| Polymer A | 1.15 | TEA lauryl sulfate | 0.45 | Translucent solution | 0.5 |
| Polymer A | 1.15 | TEA lauryl sulfate | 1.00 | Translucent solution | 1.2 |
| Polymer A | 1.15 | TEA lauryl sulfate | 2.40 | Translucent solution | 2.8 |
| Polymer A | 1.15 | TEA lauryl sulfate | 4.80 | Translucent solution | 5.5 |
| Polymer B | 4.26 | TEA lauryl sulfate | 0.20 | Translucent solution | 0.9 |
| Polymer B | 4.26 | TEA lauryl sulfate | 0.50 | Translucent solution | 2.1 |
| Polymer B | 4.26 | TEA lauryl sulfate | 1.00 | Slight whitish cloud | 4.3 |
| Polymer B | 4.26 | TEA lauryl sulfate | 1.30 | Slight whitish cloud | 5.5 |
| Polymer C | 6.2 | TEA lauryl sulfate | 0.20 | Insoluble particles | 1.2 |
| Polymer C | 6.2 | TEA lauryl sulfate | 0.45 | Insoluble particles | 2.8 |
| Polymer C | 6.2 | TEA lauryl sulfate | 0.90 | Insoluble particles | 5.6 |
| Polyquaternium 7* | 1.4** | TEA lauryl sulfate | 1.00 | Translucent solution | 1.4 |
| Polyquaternium 7* | 1.4** | TEA lauryl sulfate | 1.50 | Translucent solution | 2.1 |
| Polyquaternium 7* | 1.4** | TEA lauryl sulfate | 2.00 | Insoluble particles | 2.8 |

*polyquaternium 7 (Merquat 550, Nalco): DADMAC/AM Copolymer (30 mol %/70 mol %), AM = acrylamide
**measured charge density At equivalent total cationicity (around 5.5, value reached after addition of a varying quantity of polymer depending on the nature thereof), the solutions containing polymer A according to the invention have a translucent appearance, whereas the solutions comprising polymers B and C contain insoluble polymer particles. Polyquaternium 7 has a charge density which is included in the range claimed. However, after 2 g of polymer have been added to the solution, insoluble particles appear.

The invention claimed is:

1. A water-soluble copolymer comprising, by mass relative to the total mass of the copolymer:

5 to 45% of at least one cationic monomer whose cationicity comes exclusively from one or more quaternary ammonium functional groups;

50 to 95% of at least one monomer of formula (I);

$$H_2C=C\begin{matrix}R_1\\(Z)-(CH_2CH_2O)_n-R_2\end{matrix} \quad (I)$$

in which:

$R_1$ is a hydrogen atom or a methyl radical;

$Z$ is a divalent group $-C(=O)-O-$, or $-C(=O)-NH-$;

$n$ is an integer that is 2 to 200;

$R_2$ is a hydrogen atom or a carbon-containing radical which is saturated or unsaturated, optionally aromatic, linear, branched or cyclic, comprising 1 to 30 carbon atoms, and from 0 to 4 heteroatoms chosen from the group consisting of O, N and S;

the copolymer having a cationic charge density of between 0.3 and 2.6 meq/g,
wherein the copolymer also comprises at least one nonionic monomer distinct from the monomer of formula (I).

2. The copolymer according to claim 1, wherein the copolymer has a cationic charge density of between 0.5 and 1.5 meq/g.

3. The copolymer according to claim 1, wherein the monomer of formula (I) is chosen from the group consisting of:
- poly(ethylene glycol)(meth)acrylate in which $R_1$=H or $CH_3$; Z=C(=O)—O—; $R_2$=H; n=2 to 200;
- methyl-poly(ethylene glycol)(meth)acrylate, also called methoxy-poly(ethylene glycol)(meth)acrylate, in which $R_1$=H or $CH_3$; Z=C(=O)—O—; $R_2$=$CH_3$; n=2 to 200;
- alkyl-poly(ethylene glycol)(meth)acrylates in which $R_1$=H or $CH_3$; Z=C(=O)—O—; $R_2$=$C_1$-$C_{30}$ alkyl; n=2 to 200; and
- phenyl-poly(ethylene glycol)(meth)acrylates, also called poly(ethylene glycol)phenyl ether(meth)acrylate, in which $R_1$=H or $CH_3$; Z=C(=O)—O—; $R_2$=phenyl; n=2 to 200.

4. The copolymer according to claim 3, wherein the monomer of formula (I) is chosen from the group consisting of poly(ethylene glycol)(meth)acrylates and methyl-poly(ethylene glycol)(meth)acrylates, having a molar mass of between 80 and 8000 g/mol.

5. The copolymer according to claim 1, wherein the cationic monomer is chosen from the group consisting of quaternized dimethylaminoethyl acrylate (ADAME), quaternized dimethylaminoethyl methacrylate (MADAME), dimethyldiallyl ammonium chloride (DADMAC), acrylamidopropyltrimethylammonium chloride (APTAC) and methacrylamidopropyltrimethylammonium chloride (MAPTAC).

6. The copolymer according to claim 1, wherein the nonionic monomer distinct from the monomer of formula (I) represents less than 25% by mass of the copolymer.

7. The copolymer according to claim 1, wherein the nonionic monomer distinct from the monomer of formula (I) is chosen from the group consisting of acrylamide, methacrylamide, N-isopropylacrylamide, N,N-dimethylacrylamide, N-methylol acrylamide, N-vinylformamide, N-vinylacetamide, N-vinylpyridine, N-vinylpyrrolidone, acryloylmorpholine (ACMO) and diacetone acrylamide.

8. The copolymer according to claim 1, wherein all of the cationic charges of the copolymer come from quaternary ammonium functional groups.

9. The copolymer according to claim 1, which consists of, as percentage by mass relative to the total mass of the copolymer:
- 5 to 45% of at least one cationic monomer whose cationicity comes exclusively from one or more quaternary ammonium functional groups;
- 50 to 95% of at least one monomer of formula (I); and
- 5 to 25% of at least one nonionic monomer distinct from the monomer of formula (I).

10. The copolymer according to claim 1, which consists of, as percentage by mass relative to the total mass of the copolymer:
- 5 to 45% of at least one cationic monomer whose cationicity comes exclusively from one or more quaternary ammonium functional groups;
- 55 to 95% of at least one monomer of formula (I); and
- at least one nonionic monomer distinct from the monomer of formula (I).

11. The copolymer according to claim 2, wherein the monomer of formula (I) is chosen from the group consisting of:
- poly(ethylene glycol)(meth)acrylate in which $R_1$=H or $CH_3$; Z=C(=O)—O—; $R_2$=H; n=2 to 200;
- methyl-poly(ethylene glycol)(meth)acrylate, also called methoxy-poly(ethylene glycol)(meth)acrylate, in which $R_1$=H or $CH_3$; Z=C(=O)—O—; $R_2$=$CH_3$; n=2 to 200;
- alkyl-poly(ethylene glycol)(meth)acrylates in which $R_1$=H or $CH_3$; Z=C(=O)—O—; $R_2$=$C_1$-$C_{30}$ alkyl; n=2 to 200; and
- phenyl-poly(ethylene glycol)(meth)acrylates, also called poly(ethylene glycol)phenyl ether(meth)acrylate, in which $R_1$=H or $CH_3$; Z=C(=O)—O—; $R_2$=phenyl; n=2 to 200.

12. The copolymer according to claim 11, wherein the monomer of formula (I) is chosen from the group consisting of poly(ethylene glycol)(meth)acrylates and methyl-poly(ethylene glycol)(meth)acrylates, having a molar mass of between 80 and 8000 g/mol.

13. The copolymer according to claim 2, wherein the cationic monomer is chosen from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC) and methacrylamidopropyltrimethylammonium chloride (MAPTAC).

14. The copolymer according to claim 7, wherein the nonionic monomer distinct from the monomer of formula (I) represents less than 25% by mass of the copolymer.

15. The copolymer according to claim 2, wherein all of the cationic charges of the copolymer come from quaternary ammonium functional groups.

16. The copolymer according to claim 2, which consists of, as percentage by mass relative to the total mass of the copolymer:
- 5 to 45% of at least one cationic monomer whose cationicity comes exclusively from one or more quaternary ammonium functional groups;
- 50 to 95% of at least one monomer of formula (I); and
- 5 to 25% of at least one nonionic monomer distinct from the monomer of formula (I).

17. A cosmetic or detergent formulation comprising the copolymer according to claim 1.

* * * * *